(12) United States Patent
Eum et al.

(10) Patent No.: US 6,972,014 B2
(45) Date of Patent: Dec. 6, 2005

(54) OPEN SYSTEM HEAT EXCHANGE CATHETERS AND METHODS OF USE

(75) Inventors: Jay J. Eum, Irvine, CA (US); Thach Duong, Garden Grove, CA (US)

(73) Assignee: Endocare, Inc., Irvine, CA (US)

( * ) Notice: Subject to any disclaimer, the term of this patent is extended or adjusted under 35 U.S.C. 154(b) by 134 days.

(21) Appl. No.: 10/336,322

(22) Filed: Jan. 4, 2003

(65) Prior Publication Data

US 2004/0133194 A1    Jul. 8, 2004

(51) Int. Cl.$^7$ ............................................. A61B 18/18
(52) U.S. Cl. ........................ 606/21; 128/898; 607/101
(58) Field of Search ................... 606/20–31; 128/898; 607/101, 102

(56) References Cited

U.S. PATENT DOCUMENTS

| | | | |
|---|---|---|---|
| 1,011,606 A | 12/1911 | Fulton | |
| 3,087,493 A | 4/1963 | Schossow | 128/351 |
| 3,752,158 A * | 8/1973 | Kariher | 604/133 |
| 4,244,377 A | 1/1981 | Grams | 128/742 |
| 4,813,429 A | 3/1989 | Eshel | 128/736 |
| 4,823,812 A | 4/1989 | Eshel | 128/804 |
| 5,248,312 A | 9/1993 | Langberg | 606/28 |
| 5,257,977 A | 11/1993 | Eshel | 604/113 |
| 5,437,673 A * | 8/1995 | Baust et al. | 606/23 |
| 5,456,680 A | 10/1995 | Taylor | 606/2 |
| 5,460,628 A | 10/1995 | Neuwirth | 606/28 |
| 5,501,227 A | 3/1996 | Yock | 128/662.06 |
| 5,549,559 A | 8/1996 | Eshel | 604/113 |
| 5,647,868 A * | 7/1997 | Chinn | 606/21 |
| 5,827,269 A | 10/1998 | Saadat | 606/28 |
| 6,017,361 A | 1/2000 | Mikus | 607/105 |
| 6,419,690 B1 | 7/2002 | Mikus | 607/105 |

OTHER PUBLICATIONS

Onik, Ultrasound-Guided Cryosurgery, Scientific American at 62 (Jan. 1996).
Onik, Cohen, et al. Transrectal Ultrasound-Guided Percutaneous Radical Cryosurgical Ablation of the Prostate, 72 Cancer 1291 (1993).
Wong, et al. Cryosurgery as a Treatment for Prostate Carcinoma, 79 Cancer 963 (Mar. 1997).

* cited by examiner

*Primary Examiner*—Michael Peffley
(74) *Attorney, Agent, or Firm*—Lawrence N. Ginsberg

(57) ABSTRACT

Various embodiments of open system heat exchange catheters and methods of use are disclosed. The various catheters can be used with various ablative surgical devices. One specific exemplary use is in conjunction with cryosurgical probes involving ablation of the prostate, in which the integrity of the urethra is desired to be maintained. Other uses involve various heating ablative devices. In one embodiment an injection tube assembly is used to provide heat exchange fluid through the urethra to the bladder where it is then expelled via a suprapubic suction tube. In other embodiments a coaxial tube assembly is utilized which defines a passageway for either expelling the bladder fluid or for providing access to an endoscope. In other embodiments a double lumen assembly is utilized that defines a passageway for expelling bladder fluid.

10 Claims, 3 Drawing Sheets

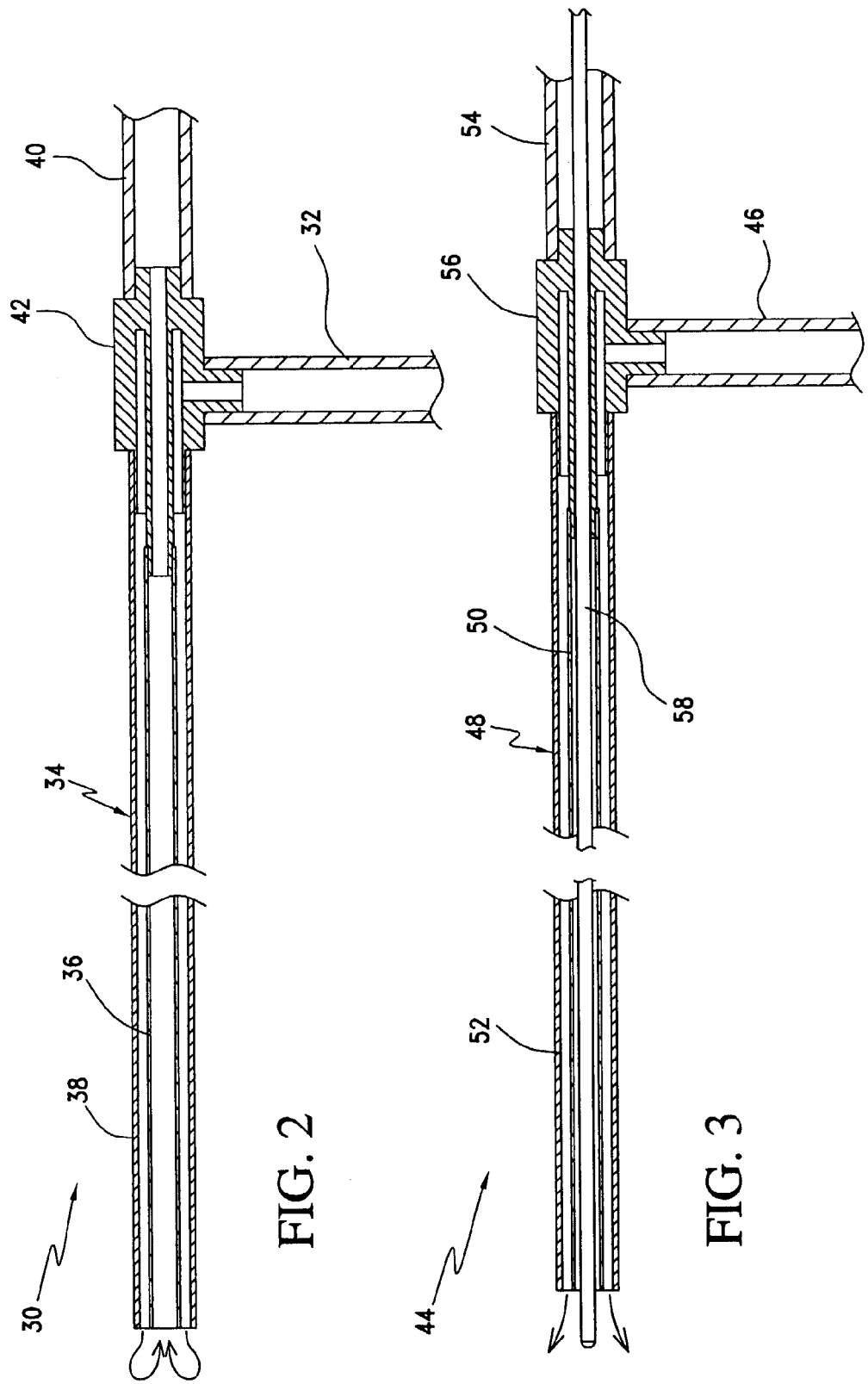

OPEN SYSTEM HEAT EXCHANGE CATHETERS AND METHODS OF USE

BACKGROUND OF THE INVENTION

1. Field of the Invention

The present invention relates to urological warming and cooling devices and more particularly to a method of warming or alternatively cooling the urethra of a patient during ablative surgery.

2. Description of the Related Art

Cryosurgical probes are used to treat a variety of diseases. The cryosurgical probes quickly freeze diseased body tissue, causing the tissue to die after which it will be absorbed by the body, expelled by the body or sloughed off. Cryothermal treatment is currently used to treat prostate cancer and benign prostate disease, breast tumors and breast cancer, liver tumors and liver cancer, lung tumors, kidney tumors, bone tumors, glaucoma and other eye diseases. Cryosurgery is also proposed for the treatment of a number of other diseases.

The use of cryosurgical probes for cryoablation of the prostate is described in Onik, *Ultrasound-Guided Cryosurgery, Scientific American* at 62 (January 1996) and Onik, Cohen, et al., *Transrectal Ultrasound-Guided Percutaneous Radial Cryosurgical Ablation Of The Prostate*, 72 Cancer 1291 (1993). In this procedure, generally referred to as cryoablation of the prostate, several cryosurgical probes are inserted through the skin in the perineal area (between the scrotum and the anus), which provides the easiest access to the prostate. The probes are pushed into the prostate gland through previously placed cannulas. Placement of the probes within the prostate gland is visualized with an ultrasound imaging probe placed in the rectum. The probes are quickly cooled to temperatures typically below –120° C. The prostate tissue is killed by the freezing, and any tumor or cancer within the prostate is also killed. The body absorbs some of the dead tissue over a period of several weeks. However, other necrosed tissue may slough off and pass through the urethra, often causing undesirable blockage. Thus, it is often desirable to avoid cryoinjury to the urethra during cryoablation of the prostate. This may be done by placing a warming catheter in the urethra and continuously flushing the catheter with warm fluid to keep the urethra from freezing.

Devices for warming the urethra have been available for quite some time. In 1911, U.S. Pat. No. 1,011,606 issued for an "Appliance For Subjecting Portions Of The Human System To Heat Or Cold." This device was a coaxial dual lumen catheter intended for the application of therapeutic cooling or heating to the urethra and bladder. Devices for warming other body parts have also been proposed, such as Grams, Ear Probe For Use In Closed-Loop Caloric Irrigation, U.S. Pat. No. 4,244,377 (Jan. 13, 1981), which shows a coaxial dual lumen cannula intended for the application of therapeutic heating inside the ear.

Baust, et al., Closed Circulation Tissue Warming Apparatus and Method of Using the Same in Prostate Surgery, U.S. Pat. No. 5,437,673 (Aug. 1, 1995), and related publications, illustrate use of a urethral warming catheter which is used to protect the urethra from cryothermal damage during cryosurgical treatment of the prostate for benign prostate hyperplasia. The Baust patent discloses a coaxial three lumen catheter in which warm saline passes through the outside lumen, returns through a coaxial second lumen, while the third lumen is a urinary drainage lumen centrally disposed within the other two lumens. The catheter is used to heat the urethra while the prostate is being frozen with cryosurgical probes.

Eshel, Technique for Localized Thermal Treatment of Mammals, U.S. Pat. No. 5,257,977 (Nov. 2, 1993) shows a catheter which delivers heated saline flow to provide therapeutic hyperthermia treatment of the prostate. Like the Baust patent, Eshel shows a three lumen catheter with centrally located urinary drainage lumen.

Still other devices have been described for importing fluid into the body and allowing a means for removing fluid from the body. One such device is described in Schossow, Endotracheal Tube, U.S. Pat. No. 3,087,493 (Apr. 27, 1960). Schossow describes a device employed to intubate the human trachea, such device connected with ducts and/or tubes outside the patient for the purpose of, for example, drawing off from the patient's respiratory tract undesirable liquids and/or introducing beneficial liquids into the trachea. The device consists of an outer tube, which fits inside the patient's trachea, and a two layered inner tube. The lumen of the inner tube is open to be connected with devices or ducts through which suction may be applied or fluids injected into the trachea. The distal portion of the inner tube is vented with ports or openings which create a "sprinkler" effect inside the tube. Schossow does not suggest use as a urethral warming catheter during cryoablation of the prostate.

During cryoablation, the prostate tissue is killed by freezing temperatures in the cryogenic temperature range, typically –120° C. and below. The hot fluid used for the warming catheter is supplied at about 30° C. to 50° C. Warm fluid is pumped through the urethral warming catheter, such as the catheter described in Baust. As the warm fluid travels the length of the urethral catheter disposed within the cryosurgically cooled urethra, it is cooled by the surrounding freezing tissue. By the time the hot water has traveled from the bladder neck sphincter to the external sphincter, it has been significantly cooled by the surrounding frozen prostate. As a result, the urethral tissue near the bladder neck sphincter (near the hot water outlet) is heated more than the urethral tissue near the external sphincter, creating a strong thermal gradient in the prostatic urethra and an uneven heating effect. By the time the hot water reaches the external sphincter, it may have lost so much heat to the upper region of the urethra that it is not warm enough to protect the external sphincter from freezing. In order for the tissue at the bladder neck sphincter to be adequately warmed, hotter water must be pumped in, risking urethral damage due to scalded tissue, or more water must be pumped at higher rates and pressures, increasing the material requirements of the hot water supply system and the warming catheter.

U.S. Pat. No. 6,017,361, issued to Mikus et al, entitled Urethral Warming Catheter, discloses an improved method and means for maintaining the temperature of urethral tissues during cryoablation of the prostate gland and thereby eliminates or reduces the sloughing of dead cells into the urethra. Diffuser holes or ports, much like a "sprinkler," are drilled into the inner tube of the warming catheter. The holes create an advantage over the prior art of achieving improved uniformity of fluid flow and temperature, utilizing a lower initial temperature and resulting in a more even application of thermal treatment to the urethral tissues. The apparatus may find additional utility in other areas of surgery where thermal treatment or maintenance of tissues is required with or without the capability of drainage.

SUMMARY OF THE INVENTION

The present invention includes various embodiments of open system heat exchange catheters and methods of use. The various catheters can be used with various ablative surgical devices. One specific exemplary use is in conjunction with cryosurgical probes involving ablation of the prostate, in which the integrity of the urethra is desired to be maintained. Other uses involve use with various heating ablative devices.

In one main aspect, the method for providing heat exchange with the urethra involves inserting a suprapubic suction tube into the bladder of a patient. At least one ablative surgical device is inserted into a prostate region of the patient. An injection tube assembly inserted through the patient's urethra and into the bladder. Heat exchange fluid is delivered through the injection tube assembly during operation of the at least one ablative surgical device, the heat exchange fluid is delivered into the bladder. The suction tube expels bladder fluid from the bladder during the delivering of heat exchange fluid through the injection tub assembly. The bladder fluid includes the heat exchange fluid. The urethra is warmed or alternatively cooled by the heat exchange fluid to preserve living tissue thereof.

In other embodiments, a coaxial tube assembly is used. With such an arrangement the coaxial portion can be used to define a path for the return of bladder fluid. This obviates the use of a suprapubic suction tube in providing this function. Alternatively, the use of a coaxial portion allows access for an endoscope.

In another embodiment, a double lumen tube assembly is utilized. The use of a double lumen tube assembly also obviates the need of a suprapubic suction tube by defining a path for the return of bladder fluid.

These systems are open systems inasmuch as fluid from the heat exchange catheters is not isolated from bladder fluid. Instead, it is mixed with the bladder fluid and then expelled.

BRIEF DESCRIPTION OF THE DRAWINGS

FIG. 2 is a cross-sectional view of a second embodiment of the heat exchange catheter in which a coaxial portion allows the heat exchange catheter to be used as both an inlet and an outlet for heat exchange fluid.

FIG. 3 is a cross-sectional view of a third embodiment of the heat exchange catheter in which a coaxial portion provides for the introduction of an endoscope, the heat exchange catheter being utilized with a suprapubic suction tube.

DETAILED DESCRIPTION OF THE PREFERRED EMBODIMENTS

Figure 1:
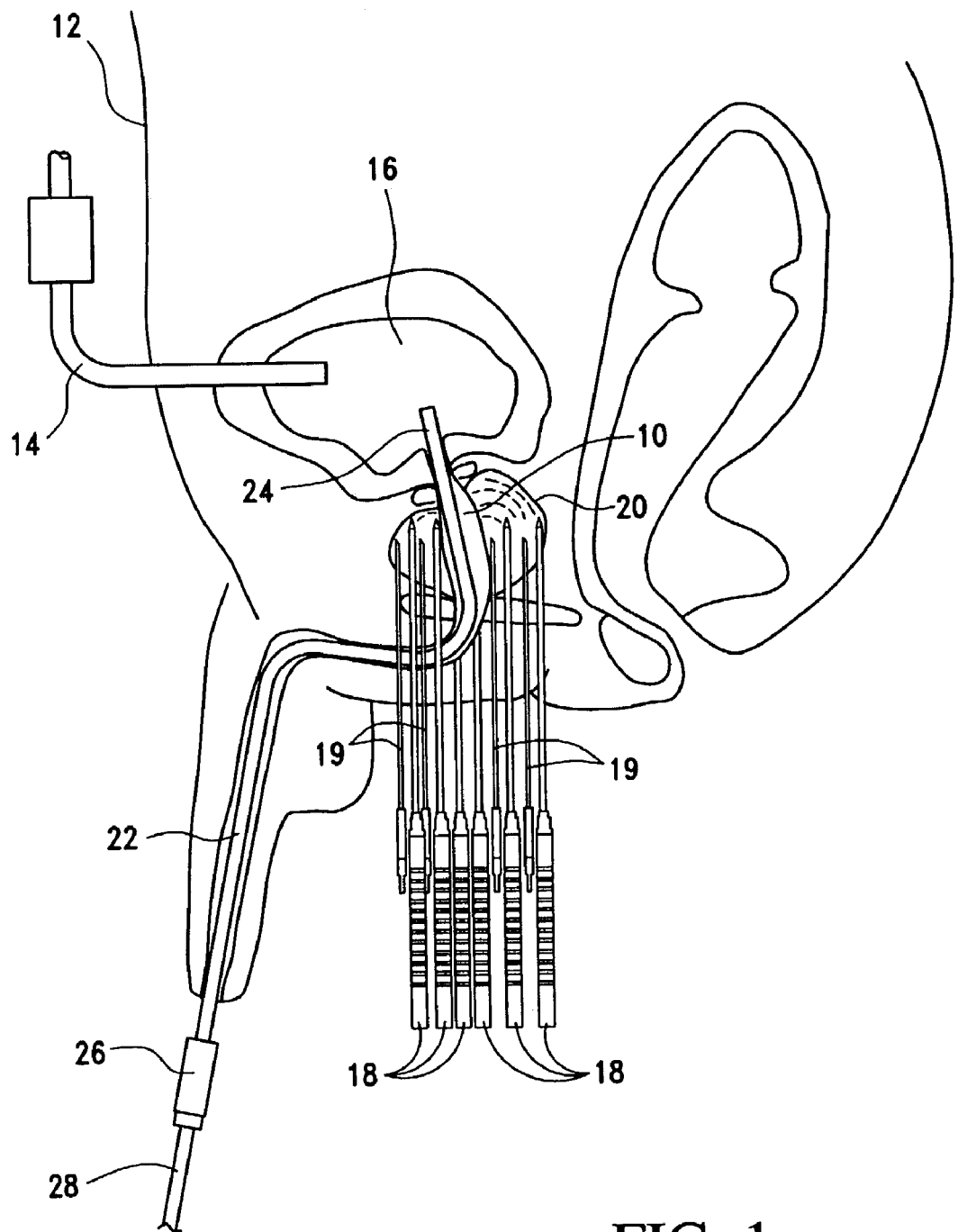
FIG. 1 is a cross-sectional view of the lower abdominal portion of the human body with a first embodiment of the heat exchange catheter in place, the first embodiment comprising an open tube, being utilized with a suprapubic suction tube.

Referring now to the drawings and the characters of reference marked thereon, FIG. 1 illustrates a first preferred method of warming a urethra 10 of a patient 12 during ablative surgery in accordance with the principles of the present invention. In this method a suprapubic suction tube 14 is inserted into the bladder 16 of the patient 12. Ablative devices 18 are inserted into the prostate region 20 of the patient 12. An injection tube assembly, designated generally as 22, is inserted through the patient's urethra 10 and into the bladder 16. Warming fluid is delivered through the injection tube assembly 22 during operation of the ablative surgical devices 18. The warming fluid is delivered into the bladder 16. The suction tube 14 is operated to expel bladder fluid from the bladder 16 during the delivering of warming fluid through the injection tub assembly 22, the bladder fluid including the warming fluid. The urethra is warmed by the warming fluid to preserve living tissue thereof.

The ablative devices are preferably cryosurgical probes such as manufactured and marketed by Endocare, Inc., of Irvine, Calif. The figure shows use of six cryosurgical probes 18 as well as four temperature probes 19. Alternatively, other ablative devices may be used, for example, radio frequency electrodes, laser fibers, microwave catheters, high-intensity focused ultrasound. In such instances the heat exchange fluid is cool so as to prevent the urethra from the heating by the ablative elements.

In this first embodiment illustrated, the injection tube assembly includes a single tube assembly including an insertable injection tube 24, a connector 26 and a source tube 28. The tubes 24 and 28 are preferably formed of a flexible material such as various plastics, including, for example, polyethelene. The connector 26 is a suitable rigid material such as polycarbonate.

Although not shown the injection tube assembly 22 receives warming fluid from a pump and warmer, which are, in turn, connected to a reservoir.

Referring now to FIG. 2 another embodiment of a warming catheter, i.e. injection tube assembly, is illustrated, designated generally as 30, in which a first section of the injection tube assembly provides delivery of warming fluid and a second section expels bladder fluid. In this embodiment, the warming catheter includes a single tube inlet 32. A coaxial portion 34 includes an inner coaxial tube 36 and an outer coaxial tube 38. The outer coaxial tube 38 is in fluid communication with the inlet 32 and discharges warming fluid into the bladder. The inner coaxial tube 36 introduces bladder fluid from the bladder. An outlet 40 is preferably a single tube that is in fluid communication with the inner tube 36. A connector 42 connects the inlet 32, the coaxial portion 34 and the outlet 40.

During use, warming fluid is delivered through the inlet 32, through the outer coaxial tube 38, thus warming the urethra, discharged to the bladder, and mixed with bladder fluid. Bladder fluid is directed through the inner coaxial tube 36 and through the outlet 40. As with the previous embodiment this system is an open system, that is, the fluid from the warming catheter 30 is discharged freely into the bladder.

Referring now to FIG. 3, another embodiment of the present invention is illustrated, designated generally by 44, in which the injection tube assembly includes a co-axial portion; however, in this embodiment, this provides access for an endoscope. As in the previous embodiment the injection tube assembly 44 includes a warming fluid inlet comprising a single tube 46. A coaxial portion 48 includes an inner coaxial tube 50 and an outer coaxial tube 52. The outer coaxial tube 52 is in fluid communication with the inlet 46 and discharges warming fluid into the bladder. However, the inner coaxial tube 50 does not introduce bladder fluid from the bladder. Instead, it retains a distal portion of an endoscope 54. An endoscope inlet 54 is preferably a single tube that is in communication with the inner tube 50 so that the endoscope inlet contains a proximal portion of the endoscope and the inner coaxial tube retains a distal portion of the endoscope. A connector 56 connects the inlet 46, the coaxial portion 48 and the endoscope inlet 54.

During use, warming fluid is delivered through the inlet 46, through the outer coaxial tube 52, thus warming the urethra, discharged to the bladder, and mixed with bladder fluid. Bladder fluid is directed through a suprapubic suction tube. The inner coaxial tube 50 and the endoscope inlet 54 cooperate to provide access to an endoscope 58. As with the previous embodiments this system is an open system, that is, the fluid from the warming catheter 30 is discharged freely into the bladder.

Figure 4:
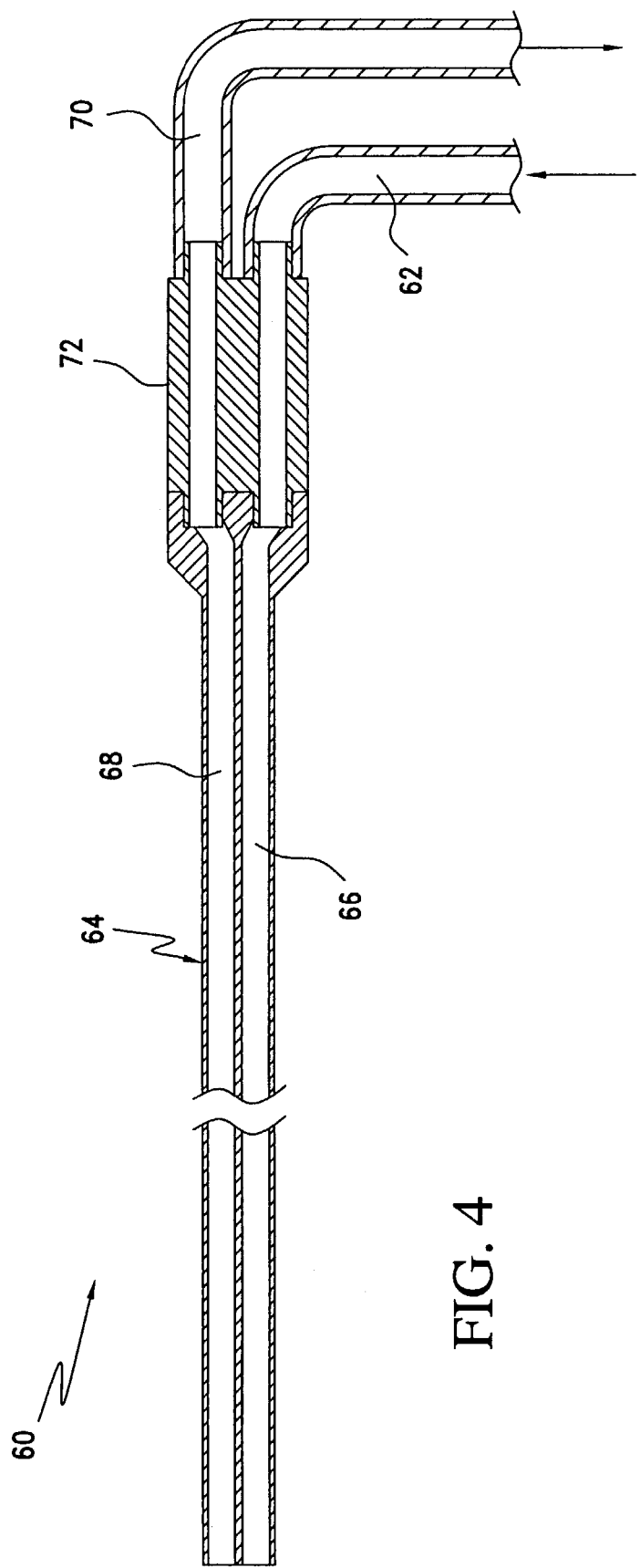
FIG. 4 is a cross-sectional view of a fourth embodiment of the heat exchange catheter in which a double lumen tube assembly provides utilization of the device as both an inlet and an outlet for heat exchange fluid.

Referring now to FIG. 4, another embodiment of the present invention is illustrated in which the injection tube assembly comprises a double lumen tube assembly, designated generally as 60. The double lumen tube assembly 60 includes a single tube inlet 62. A double lumen portion 64 includes a first fluid passageway 66 and a second fluid passageway 68. The first fluid passageway 62 is in fluid communication with the inlet 62 and discharges warming fluid into the bladder. The second fluid passageway 68 introduces bladder fluid from the bladder and directs it through a single tube outlet 70. A connector 72 is preferably used to connect the double lumen portion 64 with the inlet 62 and outlet 70.

Although the examples discussed above refer to the use of a warming fluid it is understood that if the ablative devices are for heating rather than for cooling, the heat exchange fluid would be a cooling fluid.

Thus, while the preferred embodiments of the devices and methods have been described in reference to the environment in which they were developed, they are merely illustrative of the principles of the invention. Other embodiments and configurations may be devised without departing from the spirit of the invention and the scope of the appended claims.

What is claimed is:

1. A method for warming the urethra of a patient during ablative surgery, comprising the steps of:
   a) inserting a suprapubic suction tube into the bladder of a patient;
   b) inserting at least one ablative surgical device into a prostate region of the patient;
   c) inserting an injection tube assembly through the patient's urethra and into the bladder;
   d) delivering warming fluid through said injection tube assembly during operation of said at least one ablative surgical device, said warming fluid being delivered into the bladder; and,
   e) operating said suction tube to expel bladder fluid from the bladder during said delivering of warming fluid through said injection tube assembly, said bladder fluid including said warming fluid,
   wherein said urethra is warmed by said warming fluid to preserve living tissue thereof.

2. The method of claim 1, wherein said step of inserting at least one ablative surgical device into a prostate region of the patient, comprises inserting a cryosurgical probe.

3. The method of claim 1, wherein said step of inserting an injection tube assembly comprises inserting a single tube assembly.

4. The method of claim 1, wherein said step of inserting an injection tube assembly comprises inserting a co-axial tube assembly.

5. The method of claim 1, wherein said step of inserting an injection tube assembly comprises inserting a co-axial tube assembly, a portion of said co-axial tube assembly providing access for an endoscope.

6. A method for cooling the urethra of a patient during ablative surgery, comprising the steps of:
   a) inserting a suprapubic suction tube into the bladder of a patient;
   b) inserting at least one ablative surgical device into a prostate region of the patient;
   c) inserting an injection tube assembly through the patient's urethra and into the bladder;
   d) delivering cooling fluid through said injection tube assembly during operation of said at least one ablative surgical device, said cooling fluid being delivered into the bladder; and,
   e) operating said suction tube to expel bladder fluid from the bladder during said delivering of cooling fluid through said injection tube assembly, said bladder fluid including said cooling fluid, wherein said urethra is cooling by said cooling fluid to preserve living tissue thereof.

7. The method of claim 6, wherein said step of inserting at least one ablative surgical device into a prostate region of the patient, comprises inserting a heating ablative surgical device.

8. The method of claim 6, wherein said step of inserting an injection tube assembly comprises inserting a single tube assembly.

9. The method of claim 6, wherein said step of inserting an injection tube assembly comprises inserting a co-axial tube assembly.

10. The method of claim 6, wherein said step of inserting an injection tube assembly comprises inserting a co-axial tube assembly, a portion of said co-axial tube assembly providing access for an endoscope.

* * * * *

UNITED STATES PATENT AND TRADEMARK OFFICE
CERTIFICATE OF CORRECTION

| | |
|---|---|
| PATENT NO. | : 6,972,014 B2 |
| DATED | : December 6, 2005 |
| INVENTOR(S) | : Eum et al. |

It is certified that error appears in the above-identified patent and that said Letters Patent is hereby corrected as shown below:

<u>Column 6,</u>
Line 35, delete "cooling by" and insert -- cooled by --.

Signed and Sealed this

Eleventh Day of April, 2006

JON W. DUDAS
*Director of the United States Patent and Trademark Office*